US011247951B2

(12) United States Patent
Usui et al.

(10) Patent No.: US 11,247,951 B2
(45) Date of Patent: Feb. 15, 2022

(54) METHOD FOR PRODUCING DIFLUOROETHYLENE

(71) Applicant: DAIKIN INDUSTRIES, LTD., Osaka (JP)

(72) Inventors: Takashi Usui, Osaka (JP); Tsubasa Nakaue, Osaka (JP); Yuzo Komatsu, Osaka (JP); Kazuhiro Takahashi, Osaka (JP); Takehiro Chaki, Osaka (JP); Megumi Kushida, Osaka (JP)

(73) Assignee: DAIKIN INDUSTRIES, LTD., Osaka (JP)

( * ) Notice: Subject to any disclaimer, the term of this patent is extended or adjusted under 35 U.S.C. 154(b) by 0 days.

(21) Appl. No.: 17/161,910

(22) Filed: Jan. 29, 2021

(65) Prior Publication Data

US 2021/0147323 A1 May 20, 2021

Related U.S. Application Data

(63) Continuation of application No. 16/973,991, filed as application No. PCT/JP2019/023556 on Jun. 13, 2019.

(30) Foreign Application Priority Data

Jun. 13, 2018 (JP) ................. 2018-113187

(51) Int. Cl.
C07C 17/358 (2006.01)
C07C 21/18 (2006.01)
(52) U.S. Cl.
CPC ............ C07C 17/358 (2013.01); C07C 21/18 (2013.01)
(58) Field of Classification Search
CPC .................. C07C 17/358; C07C 21/18
See application file for complete search history.

(56) References Cited

U.S. PATENT DOCUMENTS 6,281,395 B1    8/2001  Nappa et al.
8,373,010 B2    2/2013  Merkel et al.
(Continued)

FOREIGN PATENT DOCUMENTS

JP    2010-523635    7/2010
JP    2014-11665     6/2014
(Continued)

OTHER PUBLICATIONS

Craig et al., Thermodynamics of cis-trans isomerizations, (Journal of the American Chemical Society, 1961, vol. 83, pp. 3047-3050).*
(Continued)

Primary Examiner — Jafar F Parsa
(74) Attorney, Agent, or Firm — Wenderoth, Lind & Ponack, L.L.P.

(57) ABSTRACT

The present invention aims to provide an efficient method for obtaining a desired isomer of HFO-1132 from a composition comprising trans-1,2-difluoroethylene (HFO-1132 (E)) and cis-1,2-difluoroethylene (HFO-1132(Z)). The present invention provides, as a means for solving the problem, a method for producing HFO-1132(E) and/or HFO-1132(Z), comprising steps (1) to (3): (1) supplying a composition comprising HFO-1132(E) and/or HFO-1132(Z) to a reactor filled with a catalyst to perform an isomerization reaction between the HFO-1132(E) and the HFO-1132(Z); (2) separating the reaction product obtained in step (1) into a first stream comprising the HFO-1132(E) as a main component, and a second stream comprising the HFO-1132(Z) as a main component; and (3) recycling the first stream or the second stream obtained in step (2) to the reactor, to subject the first stream or the second stream to the isomerization reaction.

11 Claims, 3 Drawing Sheets

(56) References Cited

U.S. PATENT DOCUMENTS

| | | | |
|---|---|---|---|
| 2008/0051610 A1 | 2/2008 | Wang et al. | |
| 2009/0118555 A1* | 5/2009 | Wang | C07C 17/383 |
| | | | 570/227 |

FOREIGN PATENT DOCUMENTS

| | | |
|---|---|---|
| JP | 2014-520070 | 8/2014 |
| JP | 2017-110020 | 6/2017 |
| WO | 2008/024660 | 2/2008 |
| WO | 2008/125825 | 10/2008 |
| WO | 2010/068715 | 6/2010 |
| WO | 2012/145188 | 10/2012 |
| WO | 2013/161692 | 10/2013 |

OTHER PUBLICATIONS

International Search Report dated Aug. 27, 2019 in International (PCT) Application No. PCT/JP2019/023556.

Craig et al., "Thermodynamics of cis-trans Isomerizations. The 1,2-Difluoroethylenes", Journal of the American Chemical Society, Jul. 20, 1961, vol. 83, pp. 3047-3050.

Wampler et al., "The $SO_2(^3B_1)$ Photosensitized Isomer of cis-and Trans-1,2-Difluoroethylene", International Journal of Chemical Kinetics, 1976, vol. 8, No. 4, pp. 511-517.

* cited by examiner

METHOD FOR PRODUCING DIFLUOROETHYLENE

TECHNICAL FIELD

The present disclosure relates to a method for producing difluoroethylene.

BACKGROUND ART

Non-patent Literature (NPL) 1 discloses a method for isomerizing HFO-1132(Z) to HFO-1132(E) by contacting the HFO-1132(Z) in a gas phase using iodine as a catalyst.

CITATION LIST

Non-Patent Literature

NPL 1: Journal of the American Chemical Society, 1961, Vol. 83, 3047

SUMMARY OF INVENTION

Technical Problem

An object is to provide an efficient method for obtaining HFO-1132(E) and/or HFO-1132(Z).

Solution to Problem

Item 1 A method for producing trans-1,2-difluoroethylene (HFO-1132(E)) and/or cis-1,2-difluoroethylene (HFO-1132(Z)), comprising the step of:
(1) supplying a composition comprising HFO-1132(E) and/or HFO-1132(Z) to a reactor filled with a catalyst to perform an isomerization reaction between the HFO-1132(E) and the HFO-1132(Z).

Item 2. A method for producing cis-1,2-difluoroethylene (HFO-1132(Z)), comprising the step of:
(1A) supplying trans-1,2-difluoroethylene (HFO-1132(E)) or a composition comprising HFO-1132(E) and HFO-1132(Z) to a reactor filled with a catalyst to perform an isomerization reaction between the HFO-1132(E) and the HFO-1132(Z).

Item 3. A method for producing HFO-1132(E), comprising the step of:
(1B) supplying HFO-1132(Z) or a composition comprising HFO-1132(E) and HFO-1132(Z) to a reactor filled with a catalyst to perform an isomerization reaction between the HFO-1132(E) and the HFO-1132(Z).

Item 4. The production method according to any one of Items 1 to 3,
wherein
the reaction product obtained in step (1), (1A), or (1B) comprises HFO-1132(E) and HFO-1132(Z), and
the method further comprises steps (2) and (3):
(2) separating the reaction product obtained in step (1), (1A), or (1B) into a first stream comprising the HFO-1132(E) as a main component, and a second stream comprising the HFO-1132(Z) as a main component; and
(3) recycling the first stream or the second stream obtained in step (2) to the reactor, to subject the first stream or the second stream to the isomerization reaction.

Item 5. The production method according to any one of Items 1 to 4, further comprising the step of:
(i) subjecting a halogenated ethane to a dehydrohalogenation reaction or a dehalogenation reaction to obtain a composition comprising HFO-1132(E) and HFO-1132(Z),
wherein
the composition comprising HFO-1132(E) and HFO-1132(Z) obtained in step (i) is used as the composition comprising HFO-1132(E) and HFO-1132(Z) in step (1), (1A), or (1B).

Item 6. A method for producing a composition comprising HFO-1132(E) and/or HFO-1132(Z), comprising steps (a) to (d):
(a) supplying a composition comprising hydrogen fluoride and HFO-1132(E) and/or HFO-1132(Z) to a reactor R1 filled with a catalyst to perform a fluorination reaction, thereby obtaining a reaction product comprising 1,1,2-trifluoroethane (HFC-143);
(b) supplying the reaction product obtained in step (a) to a reactor R2 filled with a catalyst to perform a dehydrofluorination reaction, thereby obtaining a reaction product comprising HFO-1132(E) and/or HFO-1132(Z);
(c) separating the reaction product obtained in step (b) into a first stream comprising the HFO-1132(E) as a main component, and a second stream comprising the HFO-1132(Z) as a main component; and
(d) recycling the first stream or the second stream obtained in step (c) to the reactor R1 to subject the first stream or the second stream to the fluorination reaction.

Item 7. A method for producing a composition comprising HFO-1132(E) and/or HFO-1132(Z), comprising steps (x) to (z): (x) supplying HFC-143 and a composition comprising HFO-1132(E) and/or HFO-1132(Z) to a reactor filled with a catalyst to perform a dehydrofluorination reaction of the HFC-143 and an isomerization reaction of the HFO-1132(E) and the HFO-1132(Z), thereby obtaining a composition comprising the HFO-1132(E) and the HFO-1132(Z);
(y) separating the reaction product obtained in step (x) into a first stream comprising the HFO-1132(E) as a main component, and a second stream comprising the HFO-1132(Z) as a main component; and
(z) recycling the first stream or the second stream obtained in step (y) to step (x), to subject the first stream or the second stream to the isomerization reaction.

Item 8. The production method according to any one of Items 1 to 7, wherein the catalyst used in step (1), (1A), (1B), (b), or (x) comprises at least one compound selected from the group consisting of halides, oxides, and oxidized halides of at least one element selected from the group consisting of Al, Mg, Ti, V, Cr, Mn, Fe, Co, Ni, Cu, Zn, Zr, Nb and Ta.

Item 9. The production method according to any one of Items 1 to 8, wherein the catalyst used in step (1), (1A), (1B), (b), or (x) comprises a fluorinated chromium oxide.

Item 10. The production method according to any one of Items 1 to 9, wherein steps (1), (1A), (1B), (b), and (x) are performed at 200° C. to 400° C.

Item 11. The production method according to any one of Items 1 to 10, wherein steps (1), (1A), (1B), (b), and (x) are performed in the presence of a diluent gas.

Item 12. The production method according to Item 11, wherein the diluent gas is at least one diluent gas selected from the group consisting of He, $N_2$, Ar, HF, and $O_2$.

Advantageous Effects of Invention

According to the present disclosure, HFO-1132(E) and/or HFO-1132(Z) can be efficiently obtained.

DESCRIPTION OF EMBODIMENTS

Figure 1:
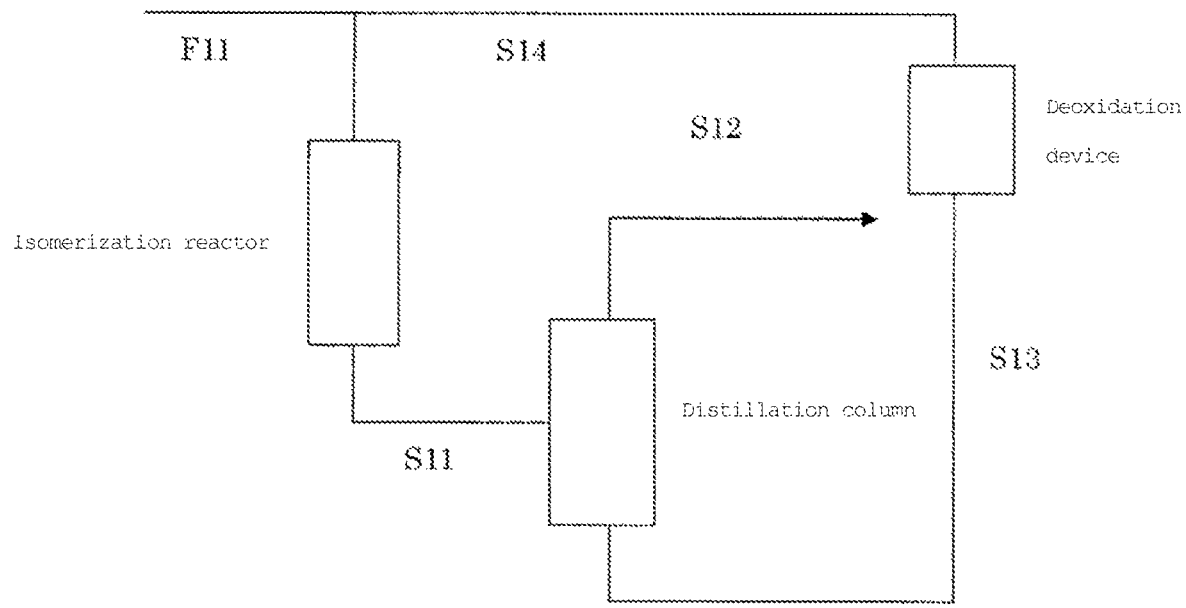
FIG. 1 schematically shows a production process of HFO-1132(E) in Example 1.

The present inventors found that in a conventional method for obtaining HFO-1132, comprising subjecting a trihalogenated ethane such as HFC-143 as a raw material to a dehydrofluorination reaction in the presence of a catalyst, the isomers HFO-1132(E) and HFO-1132(Z) are co-produced; accordingly, when only one of the isomers is desired, the other one is not required, and this is inefficient in terms of cost. The inventors also found that a conventional isomerization reaction uses iodine, which is highly corrosive and has a low sublimation point; thus, the production of equipment was difficult.

Accordingly, the present disclosure aims to provide means for solving the above problem. Specifically, an object is to provide a more efficient method for obtaining HFO-1132(E) and/or HFO-1132(Z) when the HFO-1132(E) and the HFO-1132(Z) are co-produced in, for example, a method for obtaining HFO-1132 by using a dehydrohalogenation reaction of trihalogenated ethane.

The present inventors conducted extensive research to solve the above problem, and found that isomerization in a reaction composition comprising HFO-1132 obtained by a dehydrohalogenation reaction of trihalogenated ethane is possible in the presence of a metal catalyst. The inventors also found that the above problem can be solved by combining an isomerization reaction step with a step of separating a desired isomer. The present disclosure was accomplished as a result of further research based on the above finding. The present disclosure includes the following embodiments.

1. Isomerization Reaction

An isomerization reaction between HFO-1132(E) and HFO-1132(Z) is performed. The isomerization reaction is performed according to the following reaction scheme. Since the E-isomer has a thermodynamic stability lower than that of the Z-isomer, the equilibrium is biased toward the Z-isomer. Thus, by subjecting a composition comprising HFO-1132(E) and/or HFO-1132(Z) to an isomerization reaction, a composition in which the content ratio of the HFO-1132(Z) is increased can be obtained. Such a content ratio is dependent on temperature. By performing the reaction at a higher temperature, the content of the HFO-1132(Z) is reduced, and the content of the HFO-1132(E) is increased. The reaction temperature is not limited, and can be suitably determined. From the viewpoint of yield, the reaction temperature is in the range of about 180 to 500° C., and preferably in the range of 200 to 400° C.

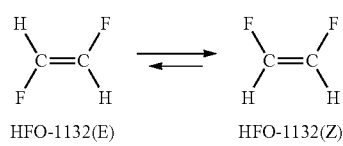

1.1. Composition Comprising HFO-1132(E) and/or HFO-1132(Z)

The composition comprising HFO-1132(E) and/or HFO-1132(Z), which is used as a raw material for isomerization, may comprise other components. The other components are not limited as long as they do not significantly impair the isomerization reaction, and can be selected from a wide variety of compounds.

Examples of other components include impurities mixed in the process of obtaining the composition comprising HFO-1132(E) and/or HFO-1132(Z), and byproducts produced in the process. The mixed impurities include impurities and the like contained in the raw material.

Examples of the method for obtaining a composition comprising HFO-1132(E) and/or HFO-1132(Z) used as a raw material include a method for subjecting a halogenated ethane to a dehydrohalogenation reaction or a dehalogenation reaction.

The halogenated ethane used in the reaction is not limited, and can be selected from a wide range. Specific examples include the halogenated ethanes described below. Such halogenated ethanes are used in a wide variety of applications, such as refrigerants, solvents, blowing agents, and propellants; and are generally commercially available.

1,1,2-Trifluoroethane ($CHF_2CH_2F$; HFC-143)
1-Bromo-1,2-difluoroethane ($CHFBrCH_2F$)
1-Chloro-1,2-difluoroethane ($CHClFCH_2F$)
1,2-Dichloro-1,2-difluoroethane ($CHClFCHClF$)
1,1,2,2-Tetrafluoroethane ($CHF_2CHF_2$)
1-Chloro-1,2,2-trifluoroethane ($CHClFCHF_2$)

1.2 Dehydrohalogenation Reaction

The dehydrohalogenation reaction is preferably performed in the presence of a catalyst. The catalyst is not limited, and can be selected from a wide variety of catalysts.

As the catalyst, known catalysts that can be used for a dehydrohalogenation reaction can be used. Examples include halides, oxides, and oxidized halides of transition metals, elements that belong to group 14 and group 15, and Mg, Al, etc. Examples of transition elements include Ti, V, Cr, Mn, Fe, Co, Ni, Cu, Zn, Zr, Nb, Ta, and W. Examples of elements that belong to group 14 include Sn and Pb. Examples of elements that belong to group 15 include Sb and Bi.

Examples of halides of these elements include fluorides and chlorides.

Of these, examples of preferable catalysts include $SbCl_5$, $SbCl_3$, $SbF_5$, $TaCl_5$, $SnCl_4$, $NbCl_5$, $FeCl_3$, $CrCl_3$, $CrF_3$, $TiCl_4$, $MoCl_5$, $Cr_2O_3$, $CrO_2$, $CrO_3$, $CoCl_2$, $NiCl_2$, $MgF_2$, AlOF (aluminum oxyfluoride), and CrOF (chromium oxyfluoride).

These catalysts can be used singly, or in a combination of two or more. Alternatively, they can be supported on a carrier. The carrier is not limited, and examples include porous alumina silicate represented by zeolite, aluminum oxide, silicon oxide, activated carbon, titanium oxide, zirconia oxide, zinc oxide, and aluminum fluoride. These can be used singly, or as a mixture thereof, or in a structural composite form thereof. Specific examples of catalysts supported on a carrier include $Cr_2O_3/Al_2O_3$, $Cr_2O_3/AlF_3$, $Cr_2O_3/C$, $CoCl_2/Cr_2O_3/Al_2O_3$, $NiCl_2/Cr_2O_3/Al_2O_3$, $CoCl_2/AlF_3$, and $NiCl_2/AlF_3$.

As a catalyst, a chromium atom-comprising catalyst is preferably used, and a chromium oxide is particularly preferable. Examples of the chromium oxide include crystalline chromium oxides, and amorphous chromium oxides. Of these, the chromium oxides subjected to fluorination are more preferable.

Examples of the method for obtaining a composition comprising HFO-1132(E) and/or HFO-1132(Z) by subjecting a halogenated ethane to a dehydrohalogenation reaction include a method for bringing HFC-143 used as a raw material into contact with a fluorinated chromium oxide used as a catalyst at 400° C. at a contact time W/Fo (cat./ml·s)=60 sec, under a 15 mol % $O_2$ atmosphere.

1.3 Dehalogenation Reaction

The dehalogenation reaction can be performed according to a known method. For example, the dehalogenation reaction can be performed by a reaction with a metal reagent such as an organomagnesium compound and zinc in an aprotic solvent.

The reaction temperature of the dehalogenation reaction is not limited, and can be suitably set. For example, the reaction temperature can be set to −20 to 200° C., and preferably 0 to 80° C.

The metals used in the dehalogenation reaction are not limited, and can be suitably determined. Usable examples include zinc, magnesium, and nickel. Of these, zinc is preferable.

1.4 Catalyst Used in Isomerization Reaction

The metal catalyst is not limited, and can be selected from a wide variety of catalysts. Although not bound by theory, it is considered that the catalyst C generates free radicals, which changes the carbon-carbon double bond to a single bond, and allows rotational motion at the double bond site, consequently causing isomerization.

1.2.1

Usable examples of metal catalysts in the isomerization reaction include the Lewis acid catalysts for use in a dehydrohalogenation reaction etc., which are shown in the section "1.2 Dehydrohalogenation Reaction."

As a catalyst, a catalyst comprising a chromium atom is preferably used, and a chromium oxide is particularly preferable. Examples of the chromium oxide include crystalline chromium oxides and amorphous chromium oxides.

There is no limitation on the chromium oxide. For example, it is preferable to use a chromium oxide represented by the composition formula $CrO_m$, wherein $1.5<m<3$, more preferably $2<m<2.75$, and even more preferably $2<m<2.3$. Chromium oxide catalysts in any form, such as powder form and pellet form, can be used, as long as they are suitable for the reaction. In particular, catalysts in the form of pellets are preferred. The above-mentioned chromium oxide catalyst can be produced, for example, by the process disclosed in Japanese Unexamined Patent Publication No. H5-146680.

Preferable catalysts include the chromium oxides mentioned above that are subjected to fluorination. The fluorinated chromium oxide can be produced by the process disclosed in Japanese Unexamined Patent Publication No. H5-146680. For example, it can be obtained by fluorinating the chromium oxide obtained by the above process with hydrogen fluoride (HF treatment). The temperature of fluorination may be, for example, about 100 to 460° C.

An example of the preparation method of a chromium oxide and an example of the preparation method of a chromium oxide catalyst are shown below. First, an aqueous solution of a chromium salt (chromium nitrate, chromium chloride, chrome alum, chromium sulfate, or the like) is mixed with aqueous ammonia to obtain a chromium hydroxide precipitate. For example, 10% aqueous ammonia can be added dropwise to a 5.7% chromium nitrate aqueous solution in an amount of 1 to 1.2 equivalents. The physical properties of chromium hydroxide can be controlled by the reaction rate of the precipitation reaction in the addition. The reaction rate is preferably fast. The reaction rate depends on the reaction solution temperature, ammonia water mixing method (mixing speed), or stirring conditions.

The precipitate is filtered, washed, and then dried. Drying is carried out, for example, in air at 70 to 200° C., more preferably at 120° C. for 1 to 100 hours, and even more preferably for 12 hours. The catalyst in this stage is called the state of chromium hydroxide. The catalyst is crushed. The precipitation reaction rate is adjusted so that the crushed product (the particle size is 1000 μm or less; products having a particle size of 46 to 1000 μm: 95%) has a powder density of 0.6 to 1.1 g/ml, and preferably 0.6 to 1.0 g/ml. When the powder density is 0.6 g/ml or more, excellent strength of the pellet is attained. When the powder density is 1.1 g/ml or less, the activity of the catalyst is sufficiently high, and the pellet is not easily cracked. The specific surface area (the specific surface area by the BET method) of the powder is 100 m/g or more, and more preferably 120 $m^2$/g or more, under degassing conditions at 200° C. for 80 minutes.

If necessary, 3 wt % or less of graphite is mixed with the powder of the chromium hydroxide to form pellets with a tableting machine. Each pellet has, for example, a diameter of 3.0 mm and a height of 3.0 mm. The crush strength (pellet strength) of the pellet is preferably 210±40 kg/$cm^2$. If this value is overly high, the gas contact efficiency is reduced, which decreases the catalytic activity, and allows the pellets to easily crack. In contrast, if the value is overly low, the pellets are easily pulverized, and are difficult to handle.

The molded catalyst is calcined in an inert gas atmosphere, for example, in a nitrogen stream, to obtain an amorphous chromium oxide. The calcination temperature is preferably 360° C. or higher; however, an overly high calcination temperature will crystalize the chromium oxide, and it is thus desirable to set the temperature to the highest temperature possible at which crystallization is still avoided. The calcination is preferably performed at 380 to 460° C., particularly 400° C., for 1 to 5 hours, and more preferably 2 hours. The specific surface area (the specific surface area by the BET method) of the sintered catalyst is 170 $m^2$/g or more, preferably 180 $m^2$/g or more, and more preferably 220 $m^2$/g or more. The upper limit of the specific surface area is, for example, about 240 $m^2$/g. When the specific surface area is 170 m/g or more, the activity of the catalyst is sufficiently high.

The fluorinated chromium oxide can then be obtained by subjecting the chromium oxide to fluorination with hydrogen fluoride (HF treatment). The fluorination temperature is preferably a temperature at which the produced water does not condense (for example, 150° C. at 1 atm), and a temperature at which the catalyst is not crystallized due to reaction heat may be set to the upper limit. The pressure in the fluorination is not limited. The fluorination is preferably performed at the pressure in the catalytic reaction. The fluorination temperature is, for example, 100 to 460° C.

In the present disclosure, it is particularly preferable to use a highly fluorinated chromium oxide catalyst comprising a large amount of fluorine. The highly fluorinated chromium oxide catalyst can be obtained by fluorinating a chromium oxide at a higher temperature than usual, for a long period of time.

The highly fluorinated chromium oxide catalyst preferably has a fluorine content of 30 weight % or more, and more preferably 30 to 45 weight %. The fluorine content can be measured by change in weight of the catalyst, or by a common chromium oxide quantitative analysis method. The specific surface area (according to the BET method) of the highly fluorinated chromium oxide catalyst is generally about 25 to 130 m$^2$/g, and preferably about 40 to 100 m$^2$/g; however, it is not limited thereto.

Although the surface area of the catalyst is decreased after fluorination treatment, the activity of the catalyst is generally higher with a larger specific surface area. The specific surface area after fluorination treatment is preferably about 25 to 130 m$^2$/g, and more preferably about 40 to 100 m$^2$/g; however, it is not limited thereto. In the present disclosure, the specific surface area is measured by the BET method.

1.5 Reaction Conditions

The reaction temperature is not limited, and can be suitably set. The reaction temperature may be in the range of about 180° C. to 500° C., and preferably in the range of about 200° C. to 400° C.

The reaction time is not limited, and can be suitably set. An increase in the contact time can raise the conversion; however, the amount of the catalyst is increased, which requires large equipment, and is thus inefficient. Accordingly, a suitable contact time can be determined. Normally, the contact time defined by the ratio of the catalyst filling amount W (g) to the flow rate Fo (flow rate at 0° C. and 1 atmosphere: cc/sec) of the raw material gas flowing to the reaction system, W/Fo, is about 10 to 80 g·sec/cc, and preferably about 20 to 60 g·sec/cc.

The pressure in the reactor is not particularly limited, and can be suitably set. However, because a high pressure promotes the formation of a polymer such as tar, a suitable pressure can be determined. The pressure is generally within the range of ordinal pressure to 0.2 MPa, and preferably within the range of ordinal pressure to about 0.1 MPa.

In the isomerization reaction, a dehydrofluorination reaction is preferably performed in the presence of a diluent gas. This will extend the catalyst life. Although not bound by theory, the catalyst life is presumably extended because the generation of a polymer and/or tar is suppressed. Examples of the diluent gas include oxygen, N$_2$ gas, helium gas, HF gas, argon gas, and the like. In particular, N$_2$ gas is preferable in view of cost.

To perform an isomerization reaction in the presence of a diluent gas, the diluent gas is supplied to a reactor. The amount of the diluent gas supplied can be suitably set. In particular, it is preferable to supply the diluent gas so that the molar ratio of the diluent gas relative to the total amount of HFO-1132(E) and HFO-1132(Z) is 0.01 to 3.0, more preferably 0.1 to 2.0, and even more preferably 0.2 to 1.0.

The gas at the outlet of the reactor may include HFO-1132a as a by-product, in addition to HFO-1132(E) and (Z), which are target products. The gas at the outlet of the reactor may further include unreacted HFC-143, and/or HFC-143a produced by the transition reaction of the raw material.

2.1 Embodiment of First Production Process of Present Disclosure

The embodiment of the first production process according to the present disclosure is a method for producing a composition comprising HFO-1132(E) and/or HFO-1132(Z), comprising steps (1) to (3):

(1) supplying a composition comprising HFO-1132(E) and/or HFO-1132(Z) to a reactor filled with a catalyst to perform an isomerization reaction between the HFO-1132(E) and the HFO-1132(Z);

(2) separating the reaction product obtained in step (1) into a first stream comprising the HFO-1132(E) as a main component, and a second stream comprising the HFO-1132(Z) as a main component; and (3) recycling the first stream or the second stream obtained in step (2) to the reactor, to subject the first or second stream to the isomerization reaction.

In the method according to this embodiment, by using the equilibrium relationship in the isomerization reaction between the HFO-1132(E) and the HFO-1132(Z), a composition comprising an increased amount of either the HFO-1132(E) or the HFO-1132(Z) can be obtained. For example, by recycling the second stream comprising the HFO-1132(Z) as a main component to step (3), a composition comprising an increased amount of HFO-1132(E) can be obtained in step (1) after recycling. Further, by recycling the second stream comprising the HFO-1132(E) as a main component to step (3), a composition comprising an increased amount of HFO-1132(Z) can be obtained in step (1) after recycling.

2.2 Step (1)

The isomerization reaction described in sections 1.4 and 1.5 can be applied to step (1).

2.3 Step (2)

In step (2), the reaction product obtained in step (1) is separated into a first stream comprising the HFO-1132(E) as a main component, and a second stream comprising the HFO-1132(Z) as a main component. More specifically, gas at the outlet of the reactor generated by the isomerization reaction in step (1) is liquefied by cooling; and then distilled off, thereby separating the gas into a first stream comprising the HFO-1132(E) as a main component, and a second stream comprising the HFO-1132(Z) as a main component.

In addition to the HFO-1132(E), which is a target compound, the first stream may comprise HFC-143a and the like, which is generated by the transition reaction of HFC-143 used as a raw material of the composition comprising HFO-1132(E) and/or HFO-1132(Z). In this case, HFO-1132(E) can be also separated by means such as additional distillation.

2.4 Step (3)

In step (3), the first stream or the second stream obtained in step (2) is recycled to the reactor, and subjected to the isomerization reaction.

To collect a composition comprising an increased amount of either the HFO-1132(E) or the HFO-1132(Z), it is preferable that the method of this embodiment further includes the step of collecting a stream (the first or second stream obtained in step (2)) that is different from a stream recycled to step (3).

3.1 Embodiment of Second Production Process of Present Disclosure

The embodiment of the second production process according to the present disclosure is a method for producing a composition comprising HFO-1132(E) and/or HFO-1132(Z), comprising steps (i) and (ii):

(i) subjecting a halogenated ethane to a dehydrohalogenation reaction or a dehalogenation reaction to obtain a composition comprising HFO-1132(E) and HFO-1132(Z); and (ii) supplying the composition comprising HFO-1132(E) and HFO-1132(Z) obtained in step (i) to a reactor filled with a metal catalyst, to perform an isomerization reaction between the HFO-1132(E) and the HFO-1132(Z).

In the method according to this embodiment, by using the equilibrium relationship in the isomerization reaction between the HFO-1132(E) and the HFO-1132(Z), a composition comprising an increased amount of HFO-1132(E) can be obtained. In step (i), a composition comprising HFO-1132(E) and HFO-1132(Z) wherein the ratio of the HFO-1132(Z) to the HFO-1132(E) is higher than the ratio according to the equilibrium relationship in the isomerization reaction between the HFO-1132(E) and the HFO-1132(Z) can be obtained. Thereafter, by performing an isomerization reaction in step (ii), a composition in which the ratio of the HFO-1132(E) is further increased in accordance with the equilibrium relationship, as compared to that before the isomerization reaction, can be obtained.

3.2 Step (i)

The conditions of step (i) can be the same as those in the method for producing a composition comprising HFO-1132 (E) and/or HFO-1132(Z) shown in sections 1.1 to 1.3.

3.3 Step (ii)

The conditions in step (ii) can be the same as those of step (1) in the embodiment of the first production process.

In step (ii), a dehydrofluorination reaction is preferably performed in the presence of a diluent gas. This will extend the catalyst life. Although not bound by theory, the catalyst life is presumably extended because the generation of a polymer and/or tar is suppressed. Examples of the diluent gas include oxygen, $N_2$ gas, helium gas, HF gas, argon gas, and the like. In particular, $N_2$ gas is preferable in view of cost.

To perform an isomerization reaction in the presence of a diluent gas, the diluent gas is supplied to a reactor. The amount of the diluent gas supplied can be suitably set. In particular, it is preferable to supply the diluent gas so that the molar ratio of the diluent gas relative to the total amount of HFO-1132(E) and HFO-1132(Z) is 0.01 to 3.0, more preferably 0.1 to 2.0, and even more preferably 0.2 to 1.0.

As in the embodiment of the first production process, the method according to this embodiment may further include steps (iii) and (iv):

(iii) separating the reaction product obtained in step (ii) into a first stream comprising the HFO-1132(E) as a main component, and a second stream comprising the HFO-1132 (Z) as a main component; and (iv) recycling the first stream or the second stream obtained in step (iii) to the reactor, to subject the first stream or the second stream to the isomerization reaction. Thus, the same effects as in the first embodiment can be obtained.

The conditions of step (iii) and (iv) can be the same as those of steps (2) and (3) in the first embodiment.

4.1 Embodiment of Third Production Process of Present Disclosure

The embodiment of the third production process according to the present disclosure is a method for producing a composition comprising HFO-1132(E) and/or HFO-1132 (Z), comprising steps (a) to (d):

(a) supplying a composition comprising HFO-1132(E) and/or HFO-1132(Z), and hydrogen fluoride to a reactor R1 filled with a catalyst to perform a fluorination reaction, thereby obtaining a reaction product comprising 1,1,2-trifluoroethane (HFC-143);

(b) supplying the reaction product obtained in step (a) to a reactor R2 filled with a catalyst to perform a dehydrofluorination reaction, thereby obtaining a reaction product comprising HFO-1132(E) and/or HFO-1132(Z);

(c) separating the reaction product obtained in step (b) into a first stream comprising the HFO-1132(E) as a main component, and a second stream comprising the HFO-1132 (Z) as a main component; and (d) recycling the first stream or the second stream obtained in step (c) to the reactor R1 to subject the first stream or the second stream to the fluorination reaction.

In the method according to this embodiment, by using the equilibrium relationship in the isomerization reaction between the HFO-1132(E) and the HFO-1132(Z), a composition comprising an increased amount of either the HFO-1132(E) or the HPO-1132(Z) can be obtained. For example, by recycling the second stream comprising HFO-1132(Z) as a main component to step (c), a composition comprising an increased amount of HFO-1132(E) can be obtained in step (b) after recycling. Further, by recycling the second stream comprising HFO-1132(E) as a main component to step (c), a composition comprising an increased amount of HFO-1132(Z) can be obtained in step (b) after recycling.

4.2 Step (a)

4.2.1 Fluorination Reaction

The fluorination reaction can be performed in a liquid phase or gas phase using a catalyst. Gas phase fluorination is preferable because a continuous reaction is possible, which increases production efficiency. Examples of the liquid phase fluorination reaction include a fluorination reaction using an antimony catalyst in HF.

4.2.2 Catalyst

Preferable examples of catalysts used in gas phase fluorination include chromium oxyfluorides, aluminum oxyfluorides, and metallic fluorides. As a catalyst, a chromium oxyfluoride catalyst is particularly preferable.

4.2.3 Reactor R1

The reactor filled with a catalyst is a reactor in the form of a fixed bed, fluidized bed, or the like filled with the catalyst mentioned above. Catalysts in the form of pellets, powders, granules, or the like can be used. The first stream comprising the HFO-1132(E) as a main component or the second stream comprising the HFO-1132(Z) as a main component each separated in step (c) is supplied to the reactor R1 to perform a fluorination reaction (HF addition reaction), thereby generating HFC-143.

4.2.4 Reaction Conditions

The reaction temperature can be in the range of 200 to 400° C., and preferably in the range of 250° C. to 350° C.

The reaction time can be suitably set, and is not limited. An increase in contact time can raise the conversion; however, the catalyst amount is increased, which requires large equipment, and is thus inefficient. Accordingly, it is necessary to select a suitable contact time. Normally, the contact time defined by the ratio of the catalyst filling amount W (g) to the flow rate Fo (flow rate at 0° C. and 1 atmosphere: cc/sec) of the raw material gas flowing to the reaction system, W/Fo, is about 10 to 80 g·sec/cc, and preferably about 20 to 60 g·sec/cc. When the content of hydrogen fluoride, which is another raw material, is equal to or larger than the stoichiometric amount, the HFO-1132(E) or the HFO-1132(Z) can be efficiently added to the HFC-143. However, considering the inhibition of catalytic degradation or the like, hydrogen fluoride can be added in an amount excess to the stoichiometric amount of HFO-1132(E) or HFO-1132(Z). The ratio of the hydrogen fluoride to the HFO-1132(E) or HFO-1132(Z) is generally about 0.5 to 20, and preferably about 1 to 10.

4.3 Step (b)

4.3.1 Catalyst

As a catalyst, those shown in section "1.2 Hydrogen Dehalogenation Reaction" can be used.

4.3.2 Reactor R2

The reactor R2 filled with a catalyst is a reactor in the form of a fixed bed, fluidized bed, or the like, filled with the catalyst mentioned above. Catalysts in the form of pellets, powders, granules, or the like can be used.

4.3.3 Reaction Conditions

The reaction temperature at which the dehydrofluorination reaction is performed is in the range of about 200 to 500° C., and preferably about 300 to 450° C.

The reaction time can be suitably set, and is not limited. An increase in contact time can raise the conversion; however, the catalyst amount is increased, which requires large equipment, and is thus inefficient. Accordingly, it is necessary to select a suitable contact time. Normally, the contact time defined by the ratio of the catalyst filling amount W (g) to the flow rate Fo (flow rate at 0° C. and 1 atmosphere: cc/sec) of the raw material gas flowing to the reaction system, W/Fo, is about 10 to 80 g·sec/cc, and preferably about 20 to 60 g·sec/cc.

An oxidizing agent can be added to prevent catalyst degradation, and typical examples include oxygen and chlorine. The amount of oxygen added can be 0.1 mol % to 20 mol % relative to HFC-143.

In step (b), the dehydrofluorination reaction is preferably performed in the presence of a diluent gas. This will extend the catalyst life. Although not bound by theory, the catalyst life is presumably extended because the generation of a polymer and/or tar is suppressed. Examples of the diluent gas include oxygen, $N_2$ gas, helium gas, HF gas, argon gas, and the like. In particular, $N_2$ gas is preferable in view of cost.

To perform a dehydrofluorination reaction in the presence of a diluent gas, an inert gas may be supplied to a reactor. The amount of the inert gas supplied can be suitably set. In particular, it is preferable to supply the inert gas so that the molar ratio of the inert gas relative to HFC-143 is 0.01 to 3.0, more preferably 0.1 to 2.0, and even more preferably 0.2 to 1.0.

4.4 Step (c)

In step (c), the reaction product obtained in step (b) is separated into a first stream comprising the HFO-1132(E) as a main component, and a second stream comprising the HFO-1132(Z) as a main component. More specifically, gas at the outlet of the reactor generated by the dehydrofluorination reaction in step (b) is liquefied by cooling; and then distilled off, thereby separating the gas into the first stream comprising the HFO-1132(E) as a main component, and the second stream comprising the HFO-1132(Z) as a main component.

In addition to the HFO-1132(E), which is a target compound, the first stream may comprise HFC-143a and the like, which is generated by the transition reaction of HFC-143 obtained in step (a). In this case, HFO-1132(E) can be separated by means such as additional distillation.

On the other hand, the second stream comprising the HFO-1132(Z) as a main component may comprise HF generated by the dehydrofluorination reaction. For the second stream, after HF is removed, the second stream is dried using a desiccant such as molecular sieve, as required; and then supplied again to the reactor used in the isomerization reaction step or the HF addition reaction step.

4.5 Step (d)

In step (d), the first stream or the second stream obtained in step (c) is recycled to the reactor R1 to subject the first stream or the second stream to the fluorination reaction.

5.1 Embodiment of Fourth Production Process of Present Disclosure

The embodiment of the fourth production process according to the present disclosure is a method for producing a composition comprising HFO-1132(E) and/or HFO-1132(Z), comprising steps (x) to (z):

(x) supplying HFC-143 and a composition comprising HFO-1132(E) and/or HFO-1132(Z) to a reactor filled with a catalyst to perform a dehydrofluorination reaction of the HFC-143 and an isomerization reaction of the HFO-1132(E) and the HFO-1132(Z), thereby obtaining a composition comprising the HFO-1132(E) and the HFO-1132(Z);

(y) separating the reaction product obtained in step (x) into a first stream comprising the HFO-1132(E) as a main component, and a second stream comprising the HFO-1132(Z) as a main component; and (z) recycling the first stream or the second stream obtained in step (y) to step (x), to subject the first or second stream to the isomerization reaction.

In the method according to this embodiment, by using the equilibrium relationship in the isomerization reaction between the HFO-1132(E) and the HFO-1132(Z), a composition comprising an increased amount of either the HFO-1132(E) or the HPO-1132(Z) can be obtained. For example, by recycling the second stream comprising the HFO-1132(Z) as a main component to step (z), a composition comprising an increased amount of HFO-1132(E) can be obtained in step (1) after recycling. Further, by recycling the second stream comprising the HFO-1132(E) as a main component to step (3), a composition comprising an increased amount of HFO-1132(Z) can be obtained in step (x) after recycling. In this embodiment, by taking advantage of the fact that the defluorination reaction of HFO-143 and the isomerization reaction of HFO-1132(E) and/or HFO-1132(Z) can be performed using a fluorinated chromium oxide as a catalyst, the same reactor can be used. This can reduce equipment cost.

5.2 Step (x)

5.2.1 Catalyst

As a catalyst, those used in the isomerization reaction, as shown in section "1.2 Hydrogen Dehalogenation Reaction," can be used. Fluorinated chromium oxides are particularly preferable.

5.2.2 Reactor R2

The reactor filled with a catalyst is a reactor in the form of a fixed bed, fluidized bed, or the like filled with a catalyst. Catalysts in the form of pellets, powders, granules, or the like can be used.

5.2.3 Reaction Conditions

The reaction temperature at which the dehydrofluorination reaction and the isomerization reaction are performed is in the range of about 200° C. to 500° C., and preferably about 300° C. to 450° C.

The reaction time can be suitably set, and is not limited. An increase in contact time can raise the conversion; however, the catalyst amount is increased, which requires large equipment, and is thus inefficient. Accordingly, it is necessary to select a suitable contact time. Normally, the contact time defined by the ratio of the catalyst filling amount W (g) to the flow rate Fo (flow rate at 0° C. and 1 atmosphere: cc/sec) of the raw material gas flowing to the reaction system, W/Fo, is about 10 to 80 g·sec/cc, and preferably about 20 to 60 g·sec/cc.

An oxidizing agent can be added to prevent catalyst degradation, and typical examples include oxygen and chlorine. The amount of oxygen added may be 0.1 mol % to 10 mol % relative to HFC-143.

In step (x), a dehydrofluorination reaction is preferably performed in the presence of a diluent gas. This will extend the catalyst life. Although not bound by theory, the catalyst life is presumably extended because the generation of a polymer and/or tar is suppressed. Examples of the diluent gas include oxygen, $N_2$ gas, helium gas, HF gas, argon gas, and the like. In particular, $N_2$ gas is preferable in view of cost.

To perform a dehydrofluorination reaction in the presence of a diluent gas, a diluent gas may be supplied to a reactor. The amount of the diluent gas supplied can be suitably set. In particular, it is preferable to supply the diluent gas so that the molar ratio of the diluent gas relative to HFC-143 is 0.01 to 3.0, more preferably 0.1 to 2.0, and even more preferably 0.2 to 1.0.

5.3 Step (y)

In step (y), the reaction product obtained in step (x) is separated into a first stream comprising the HFO-1132(E) as a main component, and a second stream comprising the HFO-1132(Z) as a main component. More specifically, gas at the outlet of the reactor generated by the isomerization reaction in step (x) is liquefied by cooling; and then distilled off, thereby separating the gas into the first stream comprising the HFO-1132(E) as a main component, and the second stream comprising HFO-1132(Z) as a main component.

In addition to the HFO-1132(E), which is a target compound, the first stream may comprise HFC-143a and the like, which is generated by the transition reaction of HFC-143 used as a raw material of the composition comprising the HFO-1132(E) and/or the HFO-1132(Z). In this case, HFO-1132(E) can be separated by means such as additional distillation.

5.4 Step (z)

In step (z), the first stream or the second stream obtained in step (y) is recycled to the reactor, and subjected to the isomerization reaction.

To collect a composition comprising an increased amount of either the HFO-1132(E) or the HFO-1132(Z), it is preferable that the method of this embodiment further includes the step of collecting a stream (the first or second stream obtained in step (y)) that is different from a stream recycled to step (z).

EXAMPLES

The present disclosure will be explained with reference to Examples below; however, the present disclosure is not limited to these Examples.

Example 1

(1) Isomerization Reaction of Trans-1,2-Difluoroethylene and/or Cis-1,2-Difluoroethylene An isomerization reaction of trans-1,2-difluoroethylene and/or cis-1,2-difluoroethylene was performed using a chromium oxyfluoride catalyst prepared by the following method, thereby obtaining a reaction composition in which either of the isomers had a concentration higher than that of the supplied raw material composition composed of trans-1,2-difluoroethylene and/or cis-1,2-difluoroethylene.

114 g of 10% ammonia water was added to 765 g of a 5.7% chromium nitrate aqueous solution. The resulting precipitate was filtered and washed, and dried in air at 120° C. for 12 hours to obtain a chromium hydroxide. The chromium hydroxide was molded into pellets each having a diameter of 3.0 mm and a height of 3.0 mm, and then calcined at 400° C. for 2 hours in a nitrogen stream. As a result of the determination of the Cr content and elemental analysis, the obtained chromium oxide was identified as $CrO_{2.0}$. The chromium oxide in the form of a pellet was supplied into a Hastelloy C reaction tube, hydrogen fluoride was diluted to 20 vol % with nitrogen, and heating was performed by gradually increasing the temperature from 200 to 360° C. When the temperature reached 360° C., fluorination was performed with 100% HF for 220 hours to obtain a fluorinated chromium oxide catalyst.

10 g of the catalyst obtained by the above method was supplied to a reactor having an outer diameter of 12.7 mm and a length of 700 mm to perform an isomerization reaction. Specifically, a raw material gas composed of 93 mol % of cis-1,2-difluoroethylene, 1.2 mol % of 1,1,1,2-tetrafluoroethane, and 3.8 mol % of 1,1,2-trifluoroethane was supplied to the reactor at a rate of 10N ml/min to perform an isomerization reaction at 250 to 300° C. Oxygen or nitrogen was added to the raw material gas to prevent degradation of the catalyst. The results of the reaction are shown in Table 1.

TABLE 1

| Reaction example | Cis-1132 (mol %) | $N_2$ (mol %) | $O_2$ (mol %) | Temperature (° C.) | Flow rate (g/ml · s) | Composition at the outlet (mol %) | | |
|---|---|---|---|---|---|---|---|---|
| | | | | | | Trans-1132 | Cis-1132 | 143a |
| 1 | 100 | 0 | 0 | 300 | 60 | 15 | 82 | 0.2 |
| 2 | 50 | 50 | 0 | 300 | 60 | 30 | 63 | 3.5 |
| 3 | 50 | 50 | 0 | 250 | 60 | 22 | 75 | 0.4 |
| 4 | 50 | 50 | 0 | 300 | 100 | 28 | 59 | 8.4 |
| 5 | 80 | 20 | 0 | 300 | 60 | 30 | 62 | 4.3 |
| 6 | 80 | 16 | 4 | 300 | 60 | 29 | 63 | 4.1 |

(2) Separation of Isomerization Reaction Composition

The composition at the outlet of the reactor obtained in the above isomerization reaction was distilled off and separated into a composition comprising trans-1,2-difluoroethylene as a main component, and a composition comprising cis-1,2-difluoroethylene as a main component. The separation was carried out using a distillation column with an inner diameter of 25 mm and a height of 2 m in which Helipack S-1 was used as a filling material. The results are shown below.

(3) Reaction Process

Figure 2:
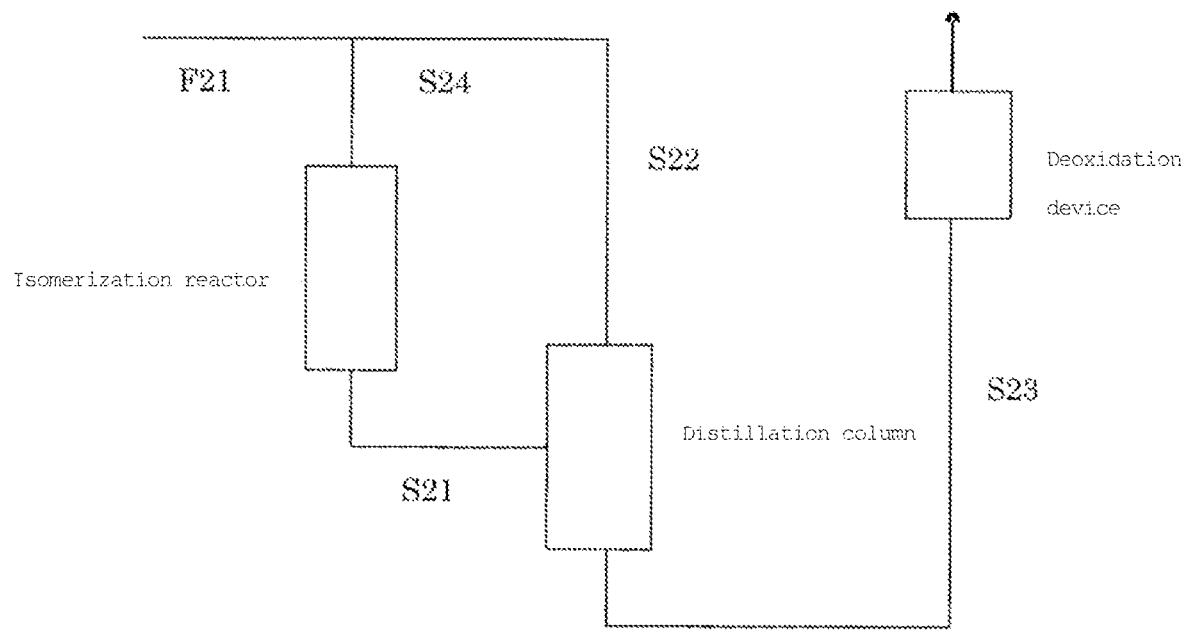
FIG. 2 schematically shows a production process of HFO-1132(Z) in Example 2.

The flow rate (kg/hr) of each component in each stream, which was obtained using the above reaction results and distillation results, is shown in Table 2. The target product is HFO-1132(E). A schematic diagram of the process is shown in FIG. 2.

TABLE 2

| Stream | F11 | S11 | S12 | S13 | S14 |
|---|---|---|---|---|---|
| | Flow rate (kg/hr) | | | | |
| HFO-1132(E) | 6.3 | 23.0 | 22.9 | 0.2 | 0.2 |
| HFO-1132(Z) | 16.6 | 60.3 | 0.1 | 60.2 | 60.2 |

The process for efficiently producing the target HFO-1132(E) alone was established.

Example 2

An isomerization reaction and separation were performed in the same manner as in Example 1, except that HFO-1132(Z) was the target product. The results are shown in Table 3. A schematic diagram of the process is shown in FIG. 2.

TABLE 3

| Stream | F21 | S21 | S22 | S23 | S24 |
|---|---|---|---|---|---|
| | | Flow rate (kg/hr) | | | |
| HFO-1132(E) | 6.3 | 8.7 | 8.7 | 0.0 | 8.7 |
| HFO-1132(Z) | 16.6 | 22.9 | 0.1 | 22.9 | 0.1 |

Example 3

A process comprising performing gas-phase fluorination of cis-1,2-difluoroethylene to obtain HFC-143, then subjecting the HFC-143 to a dehydrofluorination reaction to obtain a composition composed of trans-1,2-difluoroethylene and cis-1,2-difluoroethylene, sending the composition to a separation step to separate the composition into a stream comprising the trans-1,2-difluoroethylene as a main component and a stream comprising the cis-1,2-difluoroethylene as a main component, and recycling the cis-1,2-difluoroethylene to the fluorination reactor was established.

(1) HF Addition Reaction

Cis-1,2-difluoroethylene was supplied to a reactor (outer diameter: 12.7 mm; length: 700 mm) filled with 10 g of a catalyst obtained by the same method as in Example 1 to perform a fluorination reaction. Specifically, a raw material gas composed of 93 mol % of cis-1,2-difluoroethylene, 1.2 mol % of 1,1,1,2-tetrafluoroethane, and 3.8 mol % of 1,1,2-trifluoroethane was supplied to the reactor at a rate of 60N ml/min in total to perform a fluorination reaction. The reaction results are shown below.

TABLE 4

| Reaction Example | Z-1132 (mol %) | HF (mol %) | Temperature (° C.) | Flow rate (g/ml · s) | Composition at the outlet (mol %) | | | |
|---|---|---|---|---|---|---|---|---|
| | | | | | E-1132 | Z-1132 | 143a | 143 |
| 7 | 5.4 | 54 | 250 | 10 | 2 | 11 | 0.3 | 86 |
| 8 | 5.4 | 54 | 300 | 10 | 12 | 17 | 19 | 52 |
| 9 | 4.7 | 95 | 250 | 10 | 2 | 16 | 0.2 | 83 |
| 10 | 10.9 | 109 | 250 | 5 | 1 | 33 | 0.1 | 64 |

(2) Dehydrofluorination Reaction

The HFC-143 obtained by the above reaction was subjected to a dehydrofluorination reaction under the following conditions, thereby obtaining a composition comprising trans-1,2-difluoroethylene and cis-1,2-difluoroethylene. A reactor with an outer diameter of 12.7 mm and a length of 700 mm was filled with 10 g of a catalyst obtained by the same method as in Example 1, followed by a dehydrofluorination reaction at 350 to 400° C. Oxygen was added to the raw material gas to prevent degradation of the catalyst.

The results of the reaction are shown below.

TABLE 5

| Reaction Example | 143 (mol %) | O2 (mol %) | Temperature (° C.) | Flow rate (g/ml · s) | Composition at the outlet (mol %) | | | |
|---|---|---|---|---|---|---|---|---|
| | | | | | E-1132 | Z-1132 | 143a | 143 |
| 11 | 85 | 15 | 350 | 40 | 11 | 50 | 0.9 | 28 |
| 12 | 85 | 15 | 400 | 40 | 19 | 57 | 2.1 | 11 |
| 13 | 85 | 15 | 400 | 60 | 25 | 54 | 3.4 | 7 |
| 14 | 95 | 5 | 400 | 40 | 10 | 61 | 0.9 | 19 |

(3) Reaction Process

Figure 3:
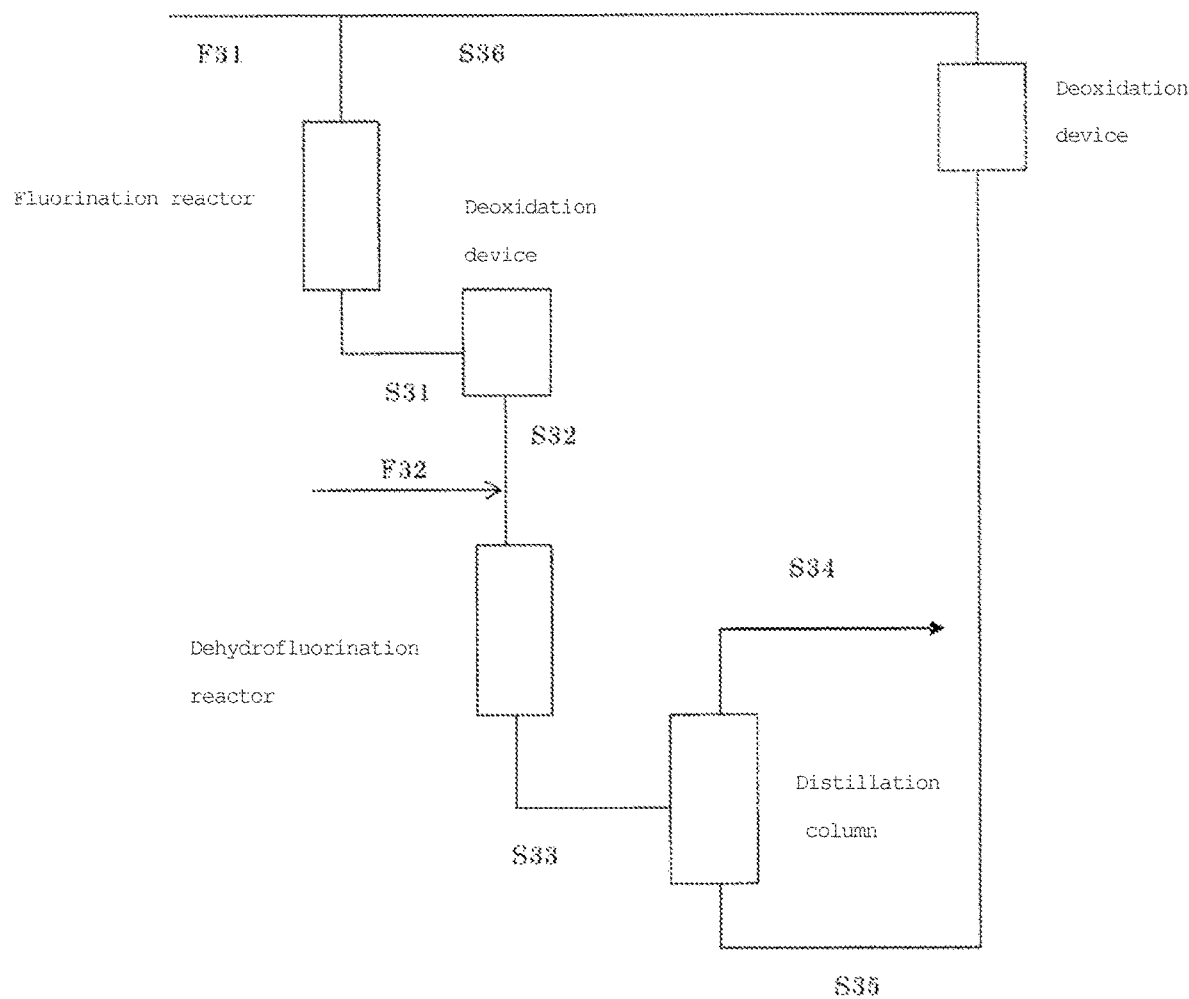
FIG. 3 schematically shows a production process of HFO-1132(E) in Example 3.

The flow rate (kg/hr) of each component in each stream obtained by using the above reaction results and distillation results is shown in Table 1 below. The target product is HFO-1132(E). HF contained in the stream is removed by a deoxidation device before the stream is sent to the next stage. Deoxidation can be performed by any of the following methods: adsorption, distillation, or water-rinsing. A schematic diagram of the process is shown in FIG. 3.

TABLE 6

| Stream | F31 | S31 | S32 | F32 | S33 | S34 | S35 | S36 |
|---|---|---|---|---|---|---|---|---|
| | | | | Flow rate (kg/hr) | | | | |
| HFO-1132 (E) | 0.0 | 0.6 | 0.6 | 0.0 | 18.0 | 18.0 | 0.0 | 0.0 |
| HFO-1132 (Z) | 0.0 | 19.8 | 19.8 | 0.0 | 59.5 | 0.0 | 59.5 | 59.5 |
| HFC-143 | 0.0 | 64.7 | 64.7 | 26.0 | 14.2 | 0.0 | 14.2 | 14.2 |
| HFC-143a | 0.0 | 0.8 | 0.8 | 0.0 | 2.8 | 2.8 | 0.0 | 0.0 |
| HF | 184.0 | 168.6 | 0.0 | 0.0 | 24.2 | 0.0 | 24.2 | 0.0 |

Example 4

A process comprising subjecting HFC-143 and cis-1,2-difluoroethylene to a dehydrofluorination reaction and an isomerization reaction to obtain a composition composed of trans-1,2-difluoroethylene and cis-1,2-difluoroethylene, sending the composition to a separation step to separate the composition into a stream comprising the trans-1,2-difluoroethylene as a main component and a stream comprising the cis-1,2-difluoroethylene as a main component, and recycling the cis-1,2-difluoroethylene to the defluorination and isomerization reactor was established.

(1) Dehydrofluorination and Isomerization

HFC-143 and cis-1,2-difluoroethylene were subjected to a dehydrofluorination reaction and an isomerization reaction under the following conditions to obtain a composition composed of trans-1,2-difluoroethylene and cis-1,2-difluoroethylene. A reactor with an outer diameter of 12.7 mm and a length of 700 mm was filled with 10 g of a catalyst obtained by the same method as in Example 1, followed by a dehydrofluorination reaction at 350° C. The results of the reaction are shown below.

TABLE 7

| Reaction Example | 143 (mol %) | Z-1132 (mol %) | Temperature (° C.) | Flow rate (g/ml · s) | Composition at the outlet (mol %) | | | |
|---|---|---|---|---|---|---|---|---|
| | | | | | E-1132 | Z-1132 | 143a | 143 |
| 15 | 40 | 60 | 350 | 40 | 13 | 56 | 1.8 | 26 |

(2) Reaction Process

Figure 4:
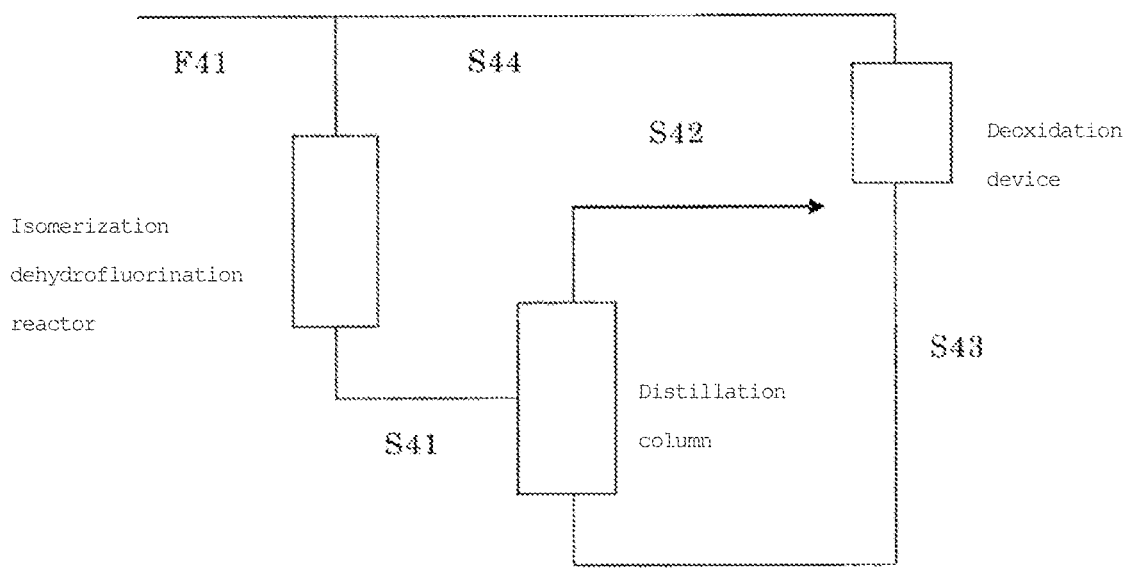
FIG. 4 schematically shows a production process of HFO-1132(E) in Example 4.

The flow rate (kg/hr) of each component in each stream obtained by using the above reaction results and distillation results is shown in Table 8 below. The target product is HFO-1132(E). HF contained in each stream is removed by a deoxidation device before the stream is sent to the next step. Deoxidation can be performed by any of the following methods: adsorption, distillation, or water-rinsing. A schematic diagram of the process is shown in FIG. 4.

TABLE 8

| Stream | F41 | S41 | S42 | S43 | S44 |
|---|---|---|---|---|---|
| | Flow rate (kg/hr) | | | | |
| HFO-1132(E) | 0.0 | 18.0 | 18.0 | 0.0 | 0.0 |
| HFO-1132(Z) | 0.0 | 78.0 | 0.3 | 77.6 | 77.6 |
| HFC-143 | 71.4 | 46.8 | 0.0 | 46.8 | 35.3 |
| HFC-143a | 0.0 | 3.4 | 3.4 | 0.0 | 0.0 |
| HF | 0.0 | 5.0 | 0.0 | 5.0 | 0.0 |

The invention claimed is:

1. A method for producing trans-1,2-difluoroethylene (HFO-1132(E)) and/or cis-1,2-difluoroethylene (HFO-1132(Z)), comprising the step of:
   (1) supplying a composition comprising HFO-1132(E) and/or HFO-1132(Z) to a reactor filled with a metal catalyst to perform an isomerization reaction between the HFO-1132(E) and the HFO-1132(Z).

2. A method for producing HFO-1132(E), comprising the step of:
   (1B) supplying HFO-1132(Z) or a composition comprising HFO-1132(E) and HFO-1132(Z) to a reactor filled with a metal catalyst to perform an isomerization reaction between the HFO-1132(E) and the HFO-1132(Z).

3. The production method according to claim 1, wherein
   the reaction product obtained in step (1) comprises HFO-1132(E) and HFO-1132(Z), and
   the method further comprises steps (2) and (3):
   (2) separating the reaction product obtained in step (1) into a first stream comprising the HFO-1132(E) as a main component, and a second stream comprising the HFO-1132(Z) as a main component; and
   (3) recycling the first stream or the second stream obtained in step (2) to the reactor, to subject the first stream or the second stream to the isomerization reaction.

4. The production method according to claim 1, further comprising the step of:
   (i) subjecting a halogenated ethane to a dehydrohalogenation reaction or a dehalogenation reaction to obtain a composition comprising HFO-1132(E) and HFO-1132(Z),
   wherein
   the composition comprising HFO-1132(E) and HFO-1132(Z) obtained in step (i) is used as the composition comprising HFO-1132(E) and HFO-1132(Z) in step (1).

5. A method for producing a composition comprising HFO-1132(E) and/or HFO-1132(Z), comprising steps (a) to (d):
   (a) supplying a composition comprising hydrogen fluoride and HFO-1132(E) and/or HFO-1132(Z) to a reactor R1 filled with a metal catalyst to perform a fluorination reaction, thereby obtaining a reaction product comprising 1,1,2-trifluoroethane (HFC-143);

(b) supplying the reaction product obtained in step (a) to a reactor R2 filled with a metal catalyst to perform a dehydrofluorination reaction, thereby obtaining a reaction product comprising HFO-1132(E) and/or HFO-1132(Z);

(c) separating the reaction product obtained in step (b) into a first stream comprising the HFO-1132(E) as a main component, and a second stream comprising the HFO-1132(Z) as a main component; and (d) recycling the first stream or the second stream obtained in step (c) to the reactor R1, to subject the first stream or the second stream to the fluorination reaction.

6. A method for producing a composition comprising HFO-1132(E) and/or HFO-1132(Z), comprising steps (x) to (z):

(x) supplying HFC-143 and a composition comprising HFO-1132(E) and/or HFO-1132(Z) to a reactor filled with a metal catalyst to perform a dehydrofluorination reaction of the HFC-143 and an isomerization reaction of the HFO-1132(E) and the HFO-1132(Z), thereby obtaining a composition comprising the HFO-1132(E) and the HFO-1132(Z);

(y) separating the reaction product obtained in step (x) into a first stream comprising the HFO-1132(E) as a main component, and a second stream comprising the HFO-1132(Z) as a main component; and (z) recycling the first stream or the second stream obtained in step (y) to step (x), to subject the first stream or the second stream to the isomerization reaction.

7. The production method according to claim 1, wherein the metal catalyst used in step (1) comprises at least one compound selected from the group consisting of halides, oxides, and oxidized halides of at least one element selected from the group consisting of Al, Mg, Ti, V, Cr, Mn, Fe, Co, Ni, Cu, Zn, Zr, Nb, and Ta.

8. The production method according to claim 1, wherein the metal catalyst used in step (1) comprises a fluorinated chromium oxide.

9. The production method according to claim 1, wherein step (1) is performed at 200° C. to 400° C.

10. The production method according to claim 1, wherein step (1) is performed in the presence of a diluent gas.

11. The production method according to claim 10, wherein the diluent gas is at least one diluent gas selected from the group consisting of He, $N_2$, Ar, HF, and $O_2$.

* * * * *